United States Patent
Wang et al.

(10) Patent No.: US 10,895,570 B2
(45) Date of Patent: Jan. 19, 2021

(54) METHOD FOR DETERMINING THE RESULT OF AN AGGLUTINATION REACTION AND MICROPLATE FOR DETERMINING PRODUCTS OF AGGLUTINATION REACTIONS

(71) Applicant: Yantai AusBio Laboratories Co., Ltd.

(72) Inventors: Zhaoqiang Wang, Yantai (CN); Wolfgang Mann, Neudrossenfeld (DE)

(73) Assignee: Yantai AusBio Laboratories Co., Ltd., Shangdong (CN)

( * ) Notice: Subject to any disclaimer, the term of this patent is extended or adjusted under 35 U.S.C. 154(b) by 166 days.

(21) Appl. No.: 15/028,421

(22) PCT Filed: Oct. 7, 2014

(86) PCT No.: PCT/EP2014/071399
§ 371 (c)(1),
(2) Date: Apr. 8, 2016

(87) PCT Pub. No.: WO2015/052162
PCT Pub. Date: Apr. 16, 2015

(65) Prior Publication Data
US 2016/0252499 A1    Sep. 1, 2016

(30) Foreign Application Priority Data
Oct. 9, 2013    (EP) .................................. 13187975

(51) Int. Cl.
*G01N 33/559*    (2006.01)
*G01N 33/53*    (2006.01)
(Continued)

(52) U.S. Cl.
CPC ........ *G01N 33/5304* (2013.01); *B01L 3/5025* (2013.01); *G01N 21/253* (2013.01);
(Continued)

(58) Field of Classification Search
USPC ........................................... 422/407; 436/809
See application file for complete search history.

(56) References Cited

U.S. PATENT DOCUMENTS 5,338,689 A * 8/1994 Yves .................. G01N 33/5304
422/504
5,491,067 A * 2/1996 Setcavage ............. B01L 3/5021
422/68.1
(Continued)

FOREIGN PATENT DOCUMENTS

EP      0797097 A1    9/1997
EP      1450159 A2    8/2004
(Continued)

OTHER PUBLICATIONS

Ashraf Agaylan et al., A highly sensitive particle agglutination assay for the detention of P53 autoantibodies in patients with lung cancer, Cancer, vol. 110, No. 11, Jan. 2007.
(Continued)

*Primary Examiner* — Christopher L Chin
(74) *Attorney, Agent, or Firm* — The Harris Firm

(57) ABSTRACT

The invention relates to a method for determining the result of an agglutination reaction and a microplate used in such a method. Agglutinated and non-agglutinated sample material is separated by means of a separation material such as gel material or a bead matrix in a centrifugation step. Whether an agglutination reaction took place or not is determined by comparing the color intensities and/or the gray levels of images of the top side and the bottom side of the respective reaction vessel. Comparing the color intensities and/or the gray levels of the two images makes the automatic determination reliable and stable. Furthermore, the reaction wells are arranged in a two-dimensional array which provides a high throughput.

12 Claims, 9 Drawing Sheets

Figure 2:
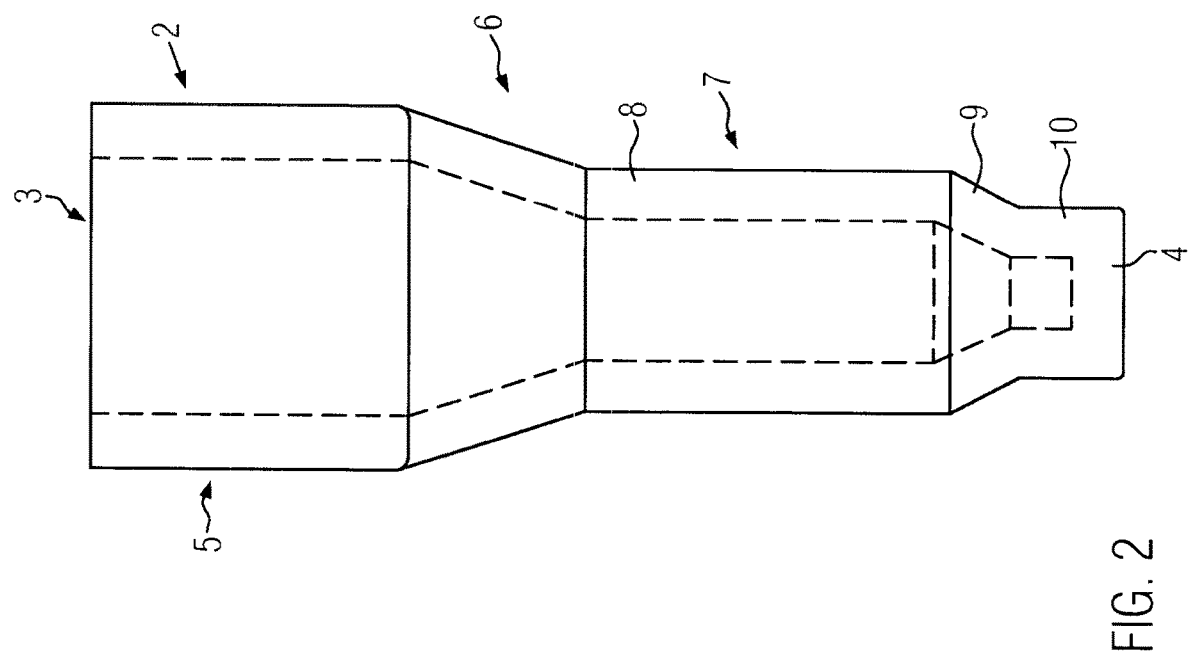

(51) Int. Cl.
  *G01N 33/543*   (2006.01)
  *G01N 21/25*    (2006.01)
  *G01N 21/82*    (2006.01)
  *B01L 3/00*     (2006.01)

(52) U.S. Cl.
  CPC ....... *G01N 21/82* (2013.01); *G01N 33/54366* (2013.01); *B01L 2200/16* (2013.01); *B01L 2300/069* (2013.01); *B01L 2300/0829* (2013.01); *B01L 2300/0858* (2013.01); *B01L 2400/0409* (2013.01)

(56) References Cited

U.S. PATENT DOCUMENTS

| | | | | |
|---|---|---|---|---|
| 5,603,899 | A | * | 2/1997 | Franciskovich .... B01L 3/50255 422/527 |
| 5,665,558 | A | * | 9/1997 | Frame ................. G01N 33/491 422/534 |
| 5,780,248 | A | * | 7/1998 | Milchanoski ........ B01L 3/5021 422/72 |
| 5,905,028 | A | * | 5/1999 | Frame ................. G01N 33/491 435/7.25 |
| 8,058,073 | B2 | * | 11/2011 | Chiapperi ............ B01L 3/5025 436/69 |
| 8,076,126 | B2 | | 12/2011 | Jakubowicz et al. |
| 10,092,901 | B2 | * | 10/2018 | Wang .................. B01L 3/50855 |
| 2004/0002415 | A1 | | 1/2004 | Jang |
| 2012/0288887 | A1 | | 11/2012 | Haga |

FOREIGN PATENT DOCUMENTS

| | | |
|---|---|---|
| EP | 2124054 A1 | 11/2009 |
| EP | 2518502 A1 | 10/2012 |
| EP | 13179437.2 | 2/2015 |
| WO | WO 95 31731 A1 | 11/1995 |
| WO | WO 2009 120516 A1 | 10/2009 |
| WO | WO 2013 117606 A1 | 8/2013 |

OTHER PUBLICATIONS

Harmening D. M. et al., Chapter 15: Alternative Techniques and Automation in Routine Blood Testing, Jan. 1, 2005, Modern Blood Banking and Transfusion Practices 5th Ed.

PCT/EP2014/071399 International Search Report, dated Apr. 23, 2015, pp. 1-6.

PCT/EP2014/071399 Written Opinion of the International Searching Authority, Patent Cooperation Treaty, dated Apr. 23, 2015, pp. 1-9.

* cited by examiner

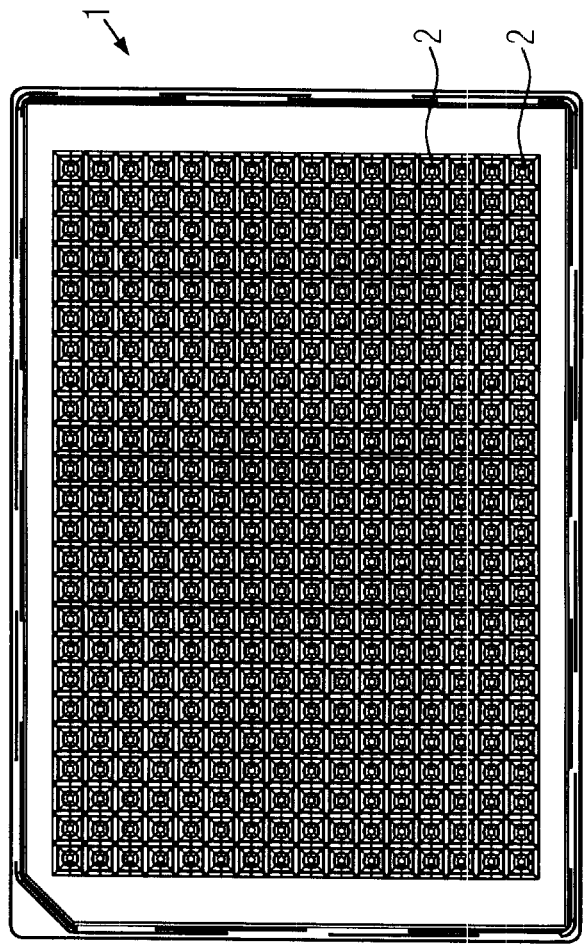
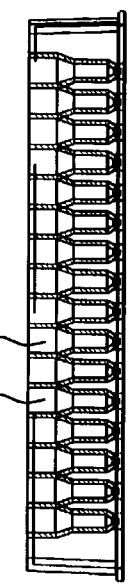
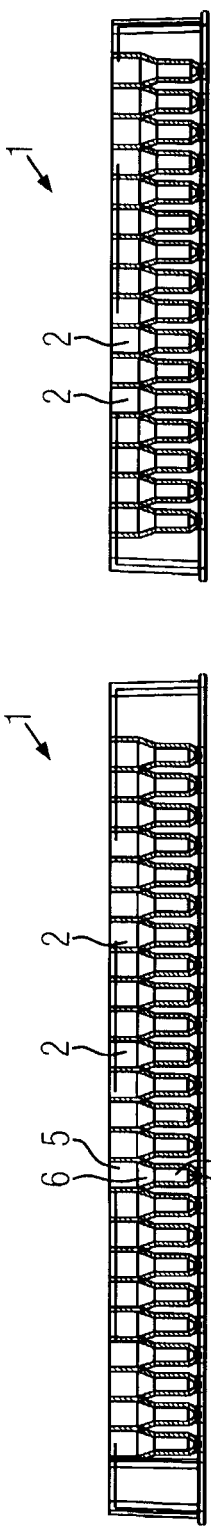
FIG. 1a
FIG. 1b
FIG. 1c

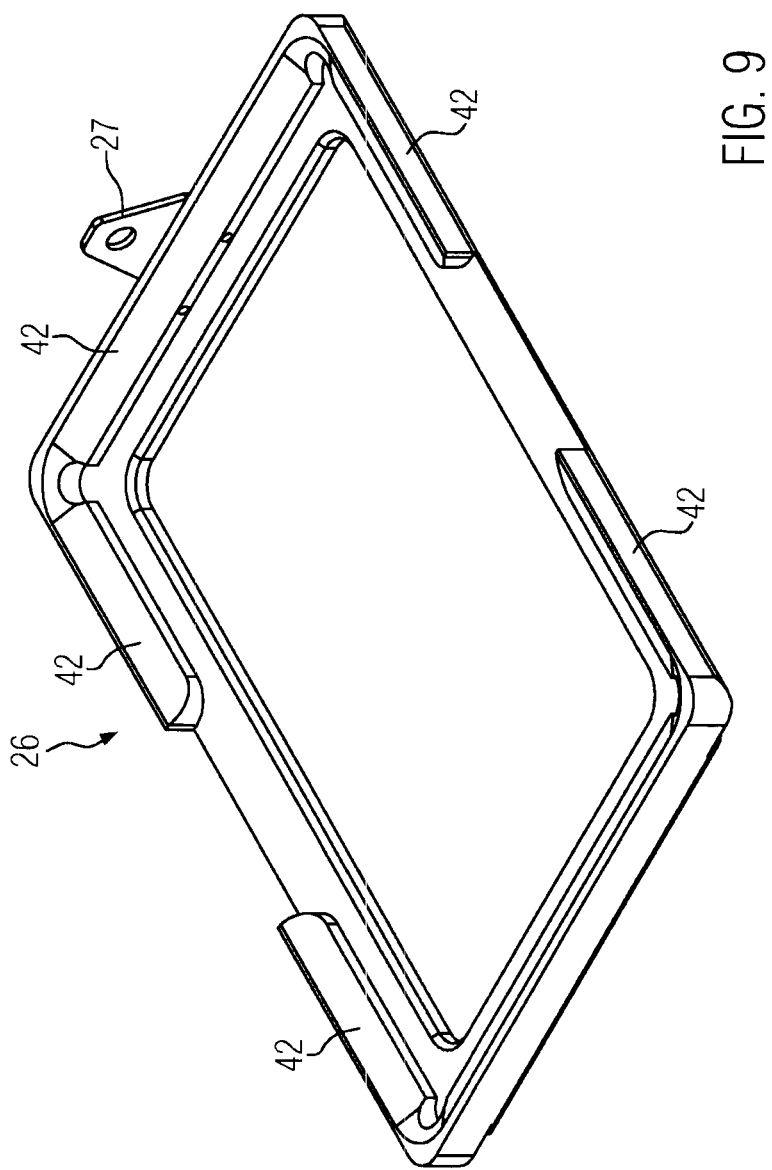

METHOD FOR DETERMINING THE RESULT OF AN AGGLUTINATION REACTION AND MICROPLATE FOR DETERMINING PRODUCTS OF AGGLUTINATION REACTIONS

CROSS REFERENCE TO PRIOR APPLICATION

This application is a National Stage Patent Application of PCT International Patent Application Ser. No. PCT/EP2014/071399 (filed on Oct. 7, 2014) under 35 U.S.C. § 371, which claims priority to European Patent Application Ser. No. EP13187975.1 (filed on Oct. 9, 2013), which are all hereby incorporated by reference in their entireties.

The present invention relates to a method for determining the result of an agglutination reaction and a microplate for determining products of agglutination reactions.

It is known to utilize test elements such as gel cards or bead cassettes for blood grouping, antigen or antibody testing, or other related immunohaematological applications or uses. These test elements commonly include a planar substrate that supports a plurality of optically transparent and vertically arranged columns or reaction wells. Each of the reaction wells retains a quantity of an inert material, such as glass beads or a gel material, that is mixed within a suspension having an antigen or antibody or is bound therewith. In use, a patient sample is placed in a reaction on top of the inert material. The sample is then incubated and centrifuged to accelerate an agglutination reaction. Red blood cells clump and are filtered by the inert material matrix. The inert material functions as filter material. The cards or cassettes comprise usually a row of columns or reaction wells and are made of a transparent material. Due to the filtering function of the gel material or bead matrix, the clumped blood cells and the undamped blood cells are separated from each other and are retained at the top of a filter material or are penetrating the filter material and reaching the bottom section of the corresponding reaction well. A row of reaction wells in which the clamped blood cells are separated from the undamped blood cells can be scanned with a camera, wherein the viewing direction of the camera is directed to the lateral side of the row of columns or reaction wells. Thus, all reaction wells can be detected simultaneously with one picture.

U.S. Pat. No. 8,076,126 B2 discloses single column test elements suitable for such a clinical testing apparatus. Each test element comprises a single reaction well having an inert material as well as a suspension containing an antigen or antibody or a carrier-bound antigen or antibody and a wrap or seal covering the reaction well. The seal is pierce-able in order to permit access to the contents of the reaction well. A cartridge is provided comprising a frame that retains a plurality of test elements, wherein the test elements are arranged in a row.

WO 95/31731 discloses a method and an apparatus for the detection of bloodgroup antigens and antibodies. Thereby immunoreactive affinity chromatography techniques are employed to detect these antigens and antibodies. The method comprises the adding of the erythrocytes to be tested to a reaction tube comprising a plurality of particles, which have immunoglobulin binding ligands like e.g. Protein A, Protein G etc. This step is followed by a centrifuging and detecting step, whereby the tube content is analyzed from a side view perspective.

D. Harmening et al. "Modern Blood Banking and Transfusion Practices", Fifth Edition, Chapter 15: "Alternative Technologies and Automation in Routine Blood Bank Testing", 1 Jan. 2005, MODERN BLOOD BANKING AND TRANSFUSION PRACTICES 5TH EDITION, F:A: DAVIS COMPANY, USA, PAGE(S) 293-302, ISBN: 0-8036-1248-6 is a review of technologies in routine blood bank testing discussing the needs and benefits of automating the known methods.

US 2012/0288887 A1 discloses a further method for a blood cell agglutination image determining and a corresponding apparatus. In this method, a microplate is used having a plurality of reaction wells being arranged in a two-dimensional array. The reaction wells comprise a bottom wall having a substantially conical shape. The inner surface of the bottom wall is formed as a tiered portion comprising a plurality of steps formed in concentric circles. In the reaction wells, agglutination reactions are carried out and, dependent on the result of the agglutination reactions, more or less step portions are covered with the reaction products. The diameter of the reaction products is optically detected by means of a camera. On the basis of the measured diameter, the result of the agglutination reaction can be automatically determined. The method comprises a centrifuging step and a tilting step for accelerating the agglutination reaction and forcing the reaction products downwards into the conical bottom wall.

Ashraf Agaylan et al. "A highly sensitive particle agglutination assay for the detection of P53 autoantibodies in patients with lung cancer", CANCER, vol. 110, no. 11, 1 Jan. 2007, pages 2502-2506, ISSN: 0008-543X, DOI: 10.1002/cncr.23057 disclose a highly sensitive and simple particle agglutination immuno-assay using super paramagnetic particles for p53 autoantibodies, p53 protein, and p53 protein-antibody complexes from large volumes of serum samples.

EP 0 797 097 A1 refers to a method for detecting an analyte in a sample liquid by agglutination, wherein the sample liquid is brought in contact with an agglutination reagent and wherein the reaction between the analyte and the agglutination reagent is determined Additionally, reaction vessels and reagents for performing said method are disclosed. For separation a compact matrix with channels having defined diameters are employed.

EP 1 450 159 A2 relates to agglutination assays and particularly to an apparatus for performing these assays. Thereby, this apparatus comprises a separation section in order to separate the agglutinates. This separation section does not make use of head-like particles or gels but rather of elements fixed to a substrate (cf. 0028]). Furthermore, EP 1 450 159 A2 discloses an automated system capable of performing an agglutination assay with increased speed and accuracy.

WO 2009/120516 A1 refers to an immunodiagnostic test including a support member, at least one test column containing a test material, and a wrap, covering the top of at least one test element. The tubes employed in WO 2009/120516 A1 are arranged in cards.

US 2004/002415 A1 relates to an automated centrifuge system for automatically centrifuging liquids containing biological materials (cf. abstract).

EP 2 124 054 A1 discloses an immunodiagnostic testing apparatus having at least one imager to provide advance agglutination evaluations during centrifugation cycle (cf. title).

An object of the present invention is to provide a method for determining the result of an agglutination reaction which can be automatically carried out, which is reliable and provides a high throughput.

A further object of the present invention is to provide a microplate which allows to carry out a method for determining the result of an agglutination reaction with a high reliability and a high throughput.

The objects of the present invention are solved by a method and a microplate as defined in the independent claims. Advantageous embodiments of the present invention are defined in the corresponding subclaims.

A method for determining the result of an agglutination reaction comprises the following steps:

- a reaction step of allowing a sample to react with a reagent in a well, wherein a microplate is used having a plurality of wells arranged in a two-dimensional array,
- a centrifugation step of rotating the microplate so that a bottom wall of the well will be arranged outwards with respect to a rotational axis, wherein in the centrifugation step an agglutinated sample material is separated from non-agglutinated sample material by means of a separation material such as a gel material or a bead matrix
- an imaging step of taking at least one image of the top side of the microplate and at least one image of the bottom side of the microplate,
- a determination step of determining the sample in said well to be positive or negative with respect to an agglutination reaction, wherein the color intensity and/or the gray level of said well in the images of the top side and the bottom side of the microplate are compared.

With this method a difference in the color intensity and/or the gray level of a certain well at the top side and the bottom side of the well is determined. Such a difference can be detected with high accuracy. Disturbing conditions, such as background light, have usually the same impact on both pictures of the top side and the bottom side of a well so that they are eliminated by comparing the color intensities and/or the gray levels of the top side and the bottom side of the corresponding reaction well. This makes the method very robust and reliable. This method is suitable for an industrial application for testing thousands or millions of samples automatically without any human intervention.

Furthermore, the provision of a two-dimensional array allows simultaneously to carry out a plurality of agglutination reactions and determination of a plurality of agglutination reactions. Due to detecting wells from the bottom side as well as from the top side, it is not necessary to use only a one-dimensional arrangement of reaction wells as it is known from e.g. U.S. Pat. No. 8,076,126 B2.

Preferably, the microplate is rotated around a horizontal axis in the centrifugation step. This facilitates the integration of the centrifugation step in an automatic system. Sample carried centrifuges having a horizontal rotational axis are described in WO 2013/1 17606 A1 and EP 13179437.2. The EP 13179437.2 is not yet published. The documents WO 2013/1 17606 A1 and EP 13179437.2 are incorporated by reference.

According to a preferred embodiment, an incubation step can be carried out before the centrifugation step for accelerating the agglutination reaction.

The reaction products, namely agglutinated probe sample parts, are separated from the reaction educts, namely non-agglutinated probe sample parts, in the centrifugation step by means of a separation material, such as a gel material or a bead matrix. The bead matrix functions as a filter material, which retains the agglutinated sample parts, particularly clamped blood cells, on the top of the bead matrix, wherein the non-agglutinated sample parts penetrate the bead matrix and are collected at the bottom portion of the corresponding well. Using a gel matrix, the non-agglutinated sample parts are separated by the agglutinated sample parts in that the non agglutinated sample parts which penetrate the gel matrix during the centrifugation step to the bottom of the reaction well, wherein the larger agglutinated sample parts are retained on the top side of the gel matrix or in the gel matrix.

The reagent can be provided on the top of the separation material or the separation material can be mixed within the suspension containing a reagent. The reagent can comprise antibodies and/or antigens which react with a predetermined sample. If the gel matrix is mixed with the reagent, the agglutination reaction takes place in the gel matrix and the agglutinated products are kept in the gel matrix, where the reaction takes place.

In case a substrate is needed in order to make an antigen/antibody reaction visible, this can be included in the gel as well. It can also be located at the bottom and the top location only.

A microplate for determining products of agglutination reactions comprises a plurality of wells arranged in a two-dimensional array, wherein at least one of said wells comprises a separation section which contains a separation material such as a gel or a bead matrix, wherein the separation section comprises at least one conical portion which is tapered downwards, so that sample material penetrating the separation material will be concentrated.

The concentration of a sample material which penetrates the separation material enhances the color intensity or gray level in the picture of the bottom side of the well, because this sample material is concentrated in the center of the reaction well. This facilitates the automatic optical analysis, it also improves the reliability of the test, because it makes it easier to compare the color intensities or grey levels of the top and bottom side of the reaction well.

The reaction wells preferably comprise a filling section at the top end of the wells, wherein the cross-sectional area of the filling section is larger than a cross-section area of the separation section.

The microplate preferably comprises at least 96 wells. Such a microplate can comprise at least 300 and particularly 384 or at least 1000 or particularly 1536 wells.

The inner height of the reaction wells is preferably in the range of 5 mm to 25 mm, and particularly 10 mm to 20 mm or 10 mm to 15 mm.

According to a further aspect of the invention, a testing apparatus comprises a centrifuge and a camera for detecting the top side of a reaction well and a further camera for detecting the bottom side of the reaction well. This testing apparatus comprises a control unit for carrying out a method as described above.

Preferably, the testing apparatus comprises a loading mechanism for horizontally loading a microplate into the centrifuge and for horizontally discharging the microplate from the centrifuge. Line cameras can be provided along the loading path of the microplates for detecting the top surface and the bottom surface of the microplate. The line cameras extend transversally to the moving direction of the microplates.

The testing apparatus preferably comprises pipetting means for automatically filling the reaction wells with a separation material such as gel material. This allows to use only the reaction wells of a microplate which are needed. Other reaction wells can be left empty. Thus, using a microplate having a plurality of reaction wells achieves a high throughput with low costs because only reaction wells are loaded with separation material and reagents which are actually used.

Figure 3:
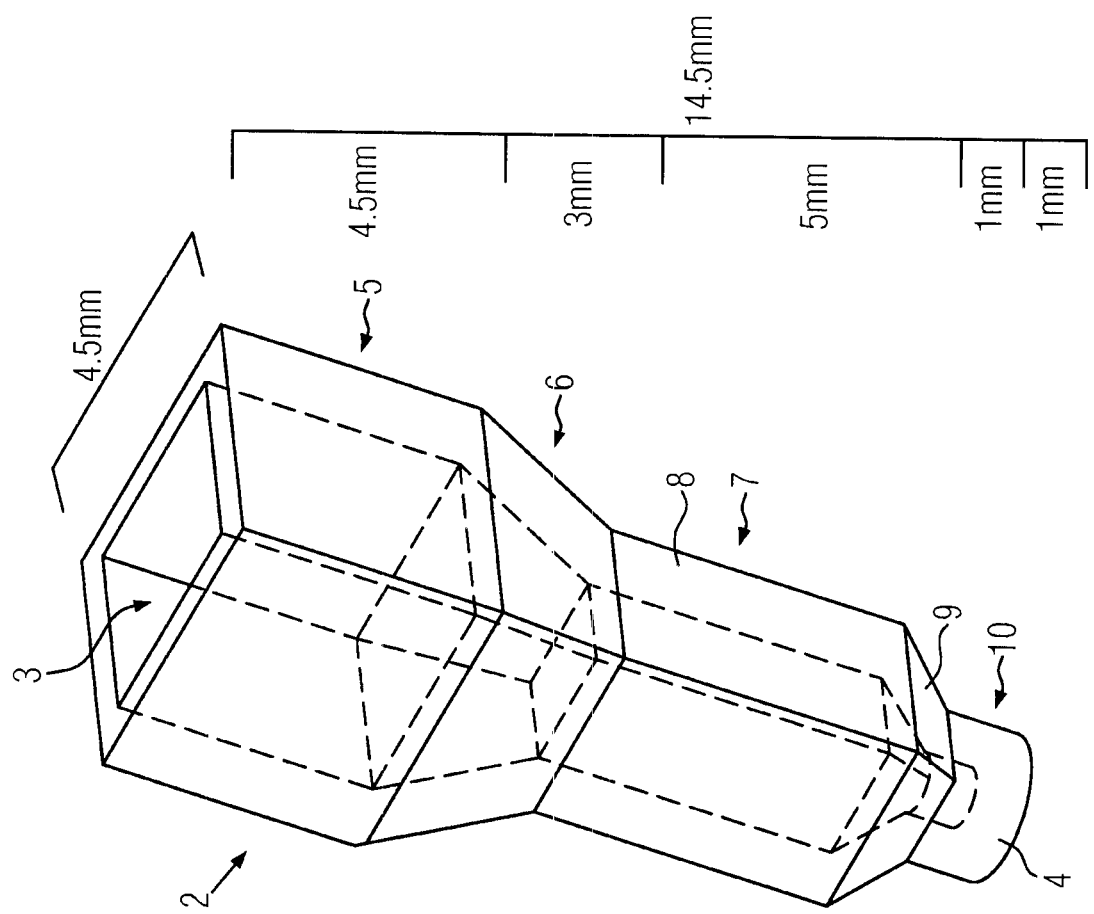
Figure 4:
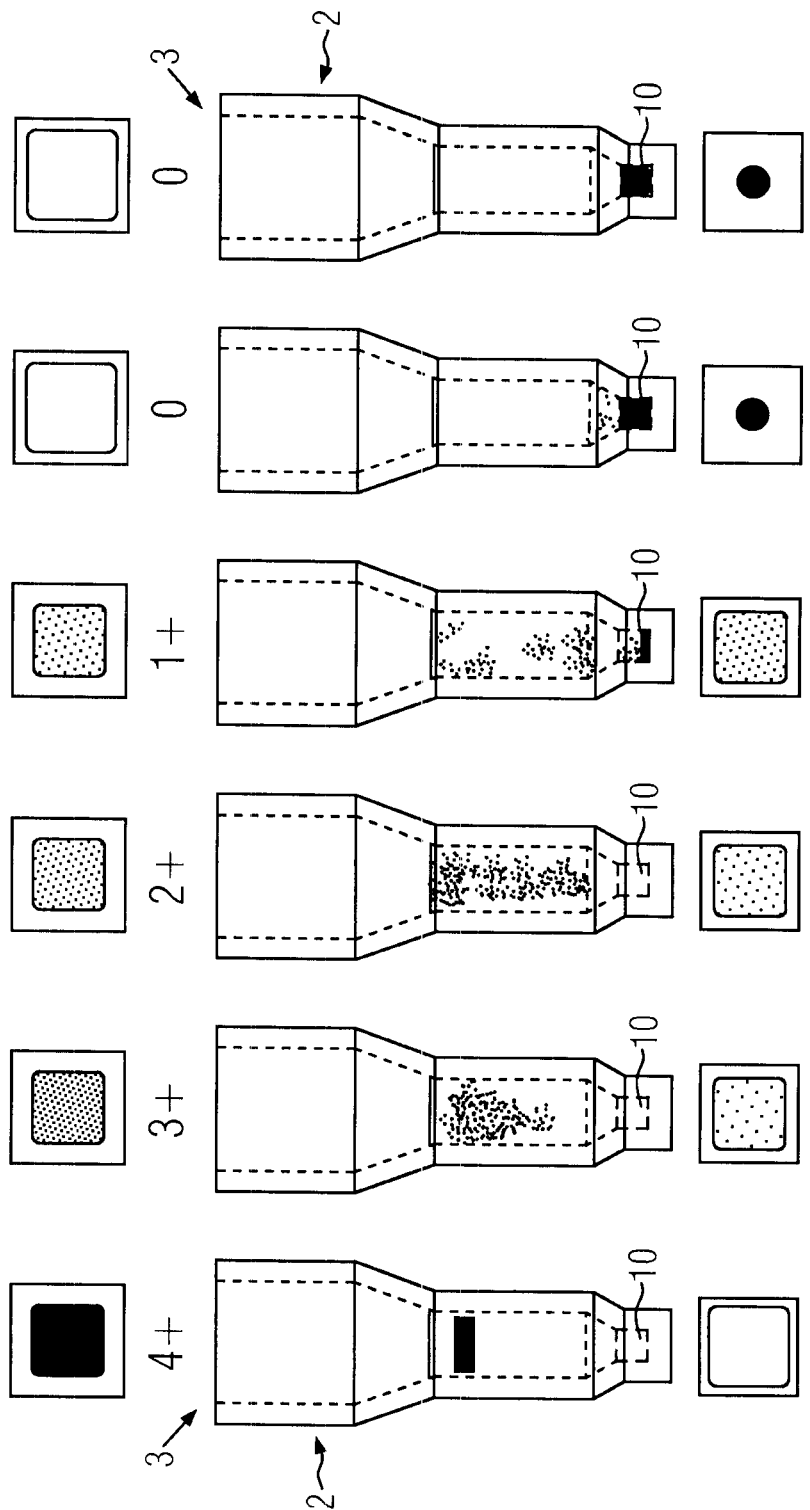

The present invention will be explained in greater detail below in conjunction with the accompanying drawings. In the drawings:

FIG. 1a is a top view of an embodiment of a microplate according to the invention, FIGS. 1b and 1c are side views of the microplate according to FIG. 1, FIG. 2 is a side view of a single reaction well of the microplate according to FIG. 1a, wherein the inner edges are depicted in dashed lines, FIG. 3 is a perspective view of a single reaction well of the microplate of FIG. 1a, FIGS. 4a-4f each reaction well containing a sample after carrying out the agglutination reaction and comprising each a picture of the well of the top side (above the well) and of the bottom side (below the well), FIGS. 5-8 an apparatus for carrying out a method for determining the result of an agglutination reaction in different views without housing, and FIG. 9 a microplate carrier.

FIGS. 1a-1c through 3 show an embodiment of a microplate 1 according to the invention. The microplate comprises 384 reaction wells 2 being arranged in a two-dimensional array of 16×24 wells.

The microplate 1 is made of a transparent, inert plastic material such as polycarbonate.

Each well 2 (FIG. 2, 3) is identical. Each reaction well 2 has an opening 3 at its top end and a bottom wall 4 at its bottom end. In the intended use, the microplate is arranged with the openings directed upwards and the bottom walls directed downwards Therefore, in the following description the term upwards is used as being directed to the opening 3 and the term downwards is used as being directed to the bottom wall 4.

The reaction well 2 comprises a filling section 5 at the top end. The filling section 5 has a cross-sectional area in the form of a square. Of course, other cross-sectional forms as circles or rectangles are possible. However, the form of a square is preferred because this allows the largest cross-section area for an arrangement with a certain density of reaction wells 2 per area. The larger the cross-section area of the filling section 5 is, the easier it is to fill the reaction well 2.

A transfer section 6 is provided below the filling section 5 which joins the filling section 5 with a separation section 7. The separation section 7 comprises a smaller cross-sectional area than the filling section 5, so that the transfer section 6 is downwardly tapered to provide a transfer from the larger cross-section area of the filling section to the smaller cross-sectional area of the separation section 7.

The separation section 7 comprises an upper part 8 in the form of a hollow cylinder. In the present embodiment, the upper part 8 has a cross-sectional area in the form of a square.

A lower part 9 of the separation section 7 is embodied as a conical portion which is tapered downwards.

The lower end of the conical portion 9 leads to a collection section 10. The collection section 10 is embodied in the form of a hollow cylinder. This hollow cylinder has a circular cross-sectional area in the present embodiment.

The cross-sectional area of the collection section 10 is substantially smaller than the cross-sectional area of the upper part 8 of the separation section 7. The lower part or conical portion 9, respectively, reduces the cross-sectional area on the upper part 8 of the separation section 7 to the collection section 10 in a ratio of at least 2:1, preferably at least 3:1 and particularly preferably at least 4:1.

A major part of the separation section is filled with the separation material, such as a gel material or a bead matrix. Such separation material is used for separating agglutinated sample parts from non-agglutinated sample parts. If agglutinated and non-agglutinated parts of a sample material are provided on the top side of the separation material and are submitted to a centrifugal force directed from the top and to the bottom end of the reaction well 2, then only the non-agglutinated parts of the sample penetrate a gel material or a filter material, such as a bead matrix. Thus, it is possible to separate agglutinated sample parts from non-agglutinated sample parts and to collect non-agglutinated sample parts in the collection section.

Due to the reduction of the cross-sectional area with respect to the upper part 8 of the separation section 7 to the collection section 10, the penetrating parts of the sample material are concentrated to the center of the reaction well. Thus, the penetrating parts of the sample material are concentrated in the small volume of the collection section 10. As a result, the collection section 10 comprises a high concentration of sample material penetrated through the separation material. Such a high concentration of sample material is advantageous for optical detection.

In the present embodiment, the height of the filling section is 4.5 mm, the height of the transfer section 6 is 3 mm, the height of the upper part 8 of the separation section 7 is 5 mm, the height of the conical portion 9 of the separation section 7 is 1 mm and the height of the collection section 10 is 1 mm.

The length of the outer edges of the filling section 5 is 4.5 mm. The wall thickness of the reaction well is about 0.7 mm.

The length of the horizontal inner edges of the upper part 8 of the separation section 7 is about 2 mm, so that the cross-sectional area of the upper part 8 of the separation section 7 is about 4 mm$^2$. The diameter of the cross-sectional area of the collection section 10 is not larger than 1 mm, so that the cross-sectional area is smaller than 1 mm$^2$.

The total inner height of the reaction well 2 which extends from the inner side of the bottom wall 4 to the top end of the reaction well 2 is 14.5 mm.

The above given numbers describe a specific example of a reaction well 2. Of course, it is possible to vary the dimensions. If the microplate 1 comprises a lower number of reaction wells 2, the cross-sectional areas of each reaction well 2 can be enlarged for a microplate with the same size.

In dependence of the kind of separation material which is used, the dimension of the height of the separation section 7 can be varied. A major part of the separation section 7 is filled with the separation material. It is also possible that the transfer section 6 and even a lower portion of the filling section 5 is filled with separation material.

As it can be seen in FIGS. 1b and 1c, the walls defining the filling section 5 are each part of two reaction wells 2 on either side of these walls.

The microplate 1 comprises a frame 11 surrounding the array of reaction wells 2. The frame 11 is supported by vertical side walls 12.

In the present embodiment, a plurality of reaction wells 2 is integrally embodied in one microplate 1. This is preferred, however, it is also possible to use single reaction wells which can be placed in a rack. The rack comprises sockets for retaining the reaction wells, wherein the sockets are preferably arranged in a two-dimensional array.

Figure 5:
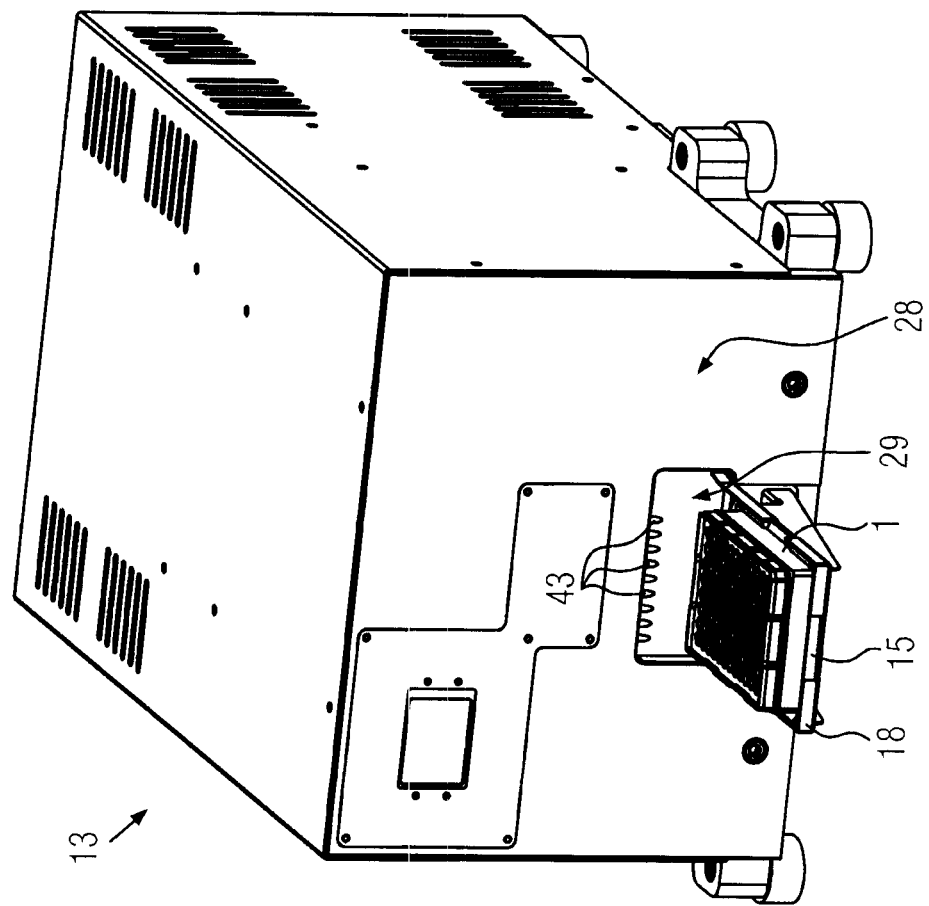

FIG. 5 shows a testing apparatus 13 for determining the result of an agglutination reaction.

Figure 6:
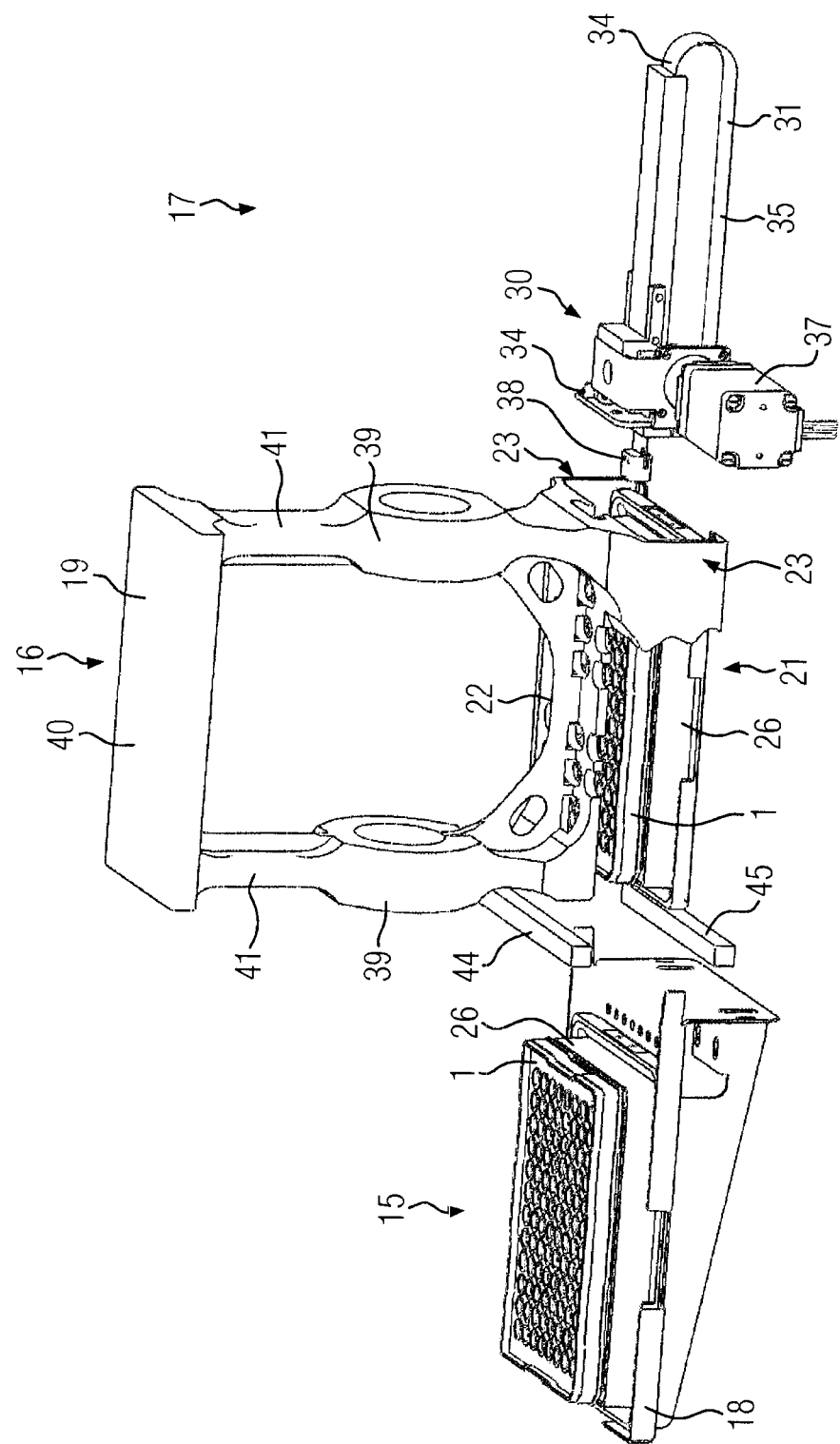

The centrifuge 14 comprises a front platform 15, a centrifuge section 16 and a driving section 17 (FIG. 6, 7, 8).

The front platform 15 has, in the top view, a rectangular form which is slightly larger than a standard microplate. Rims 18 are provided on all side edges of the front platform 15 except the one adjacent to the centrifuge section 16.

Figure 7:
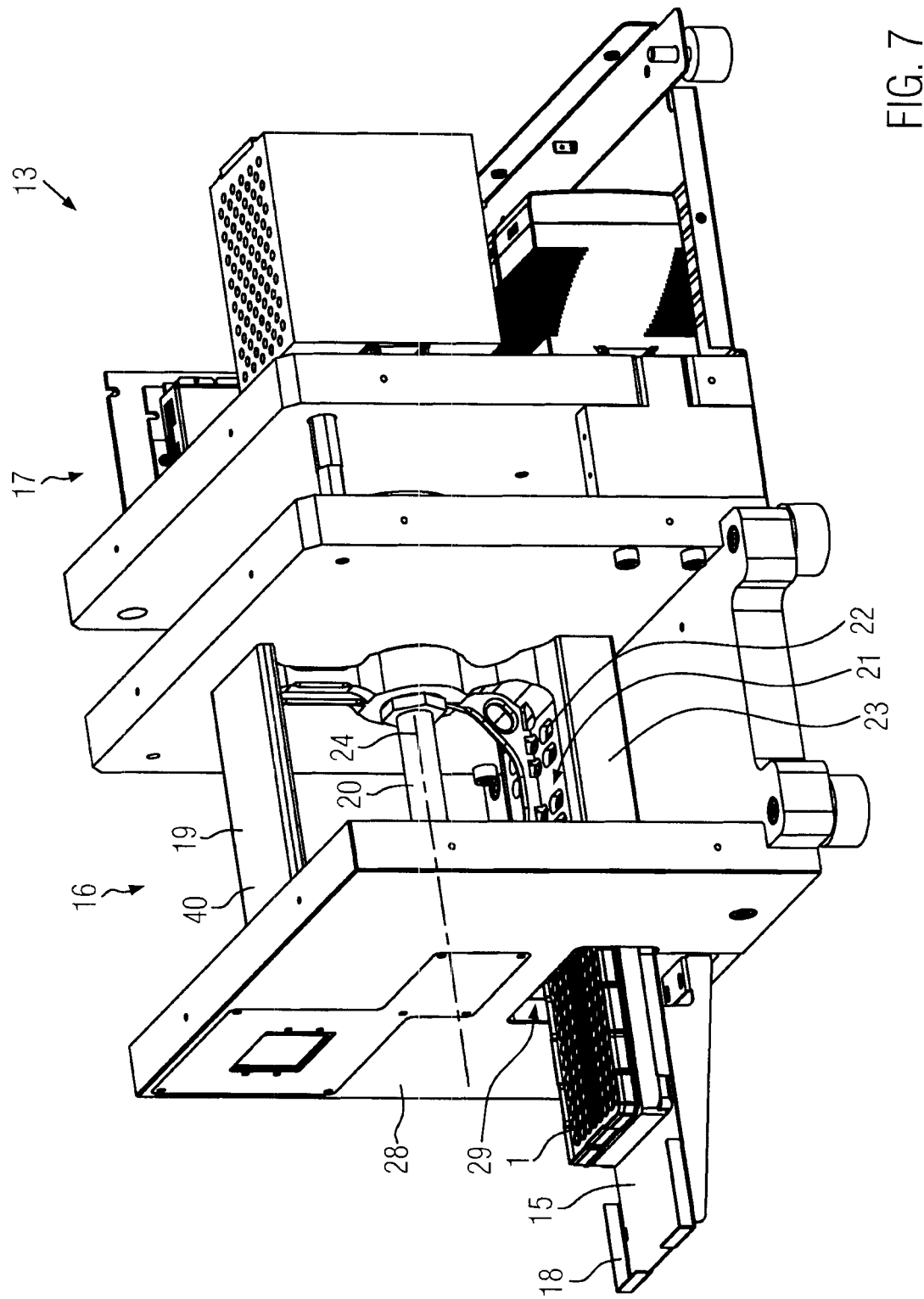
Figure 8:
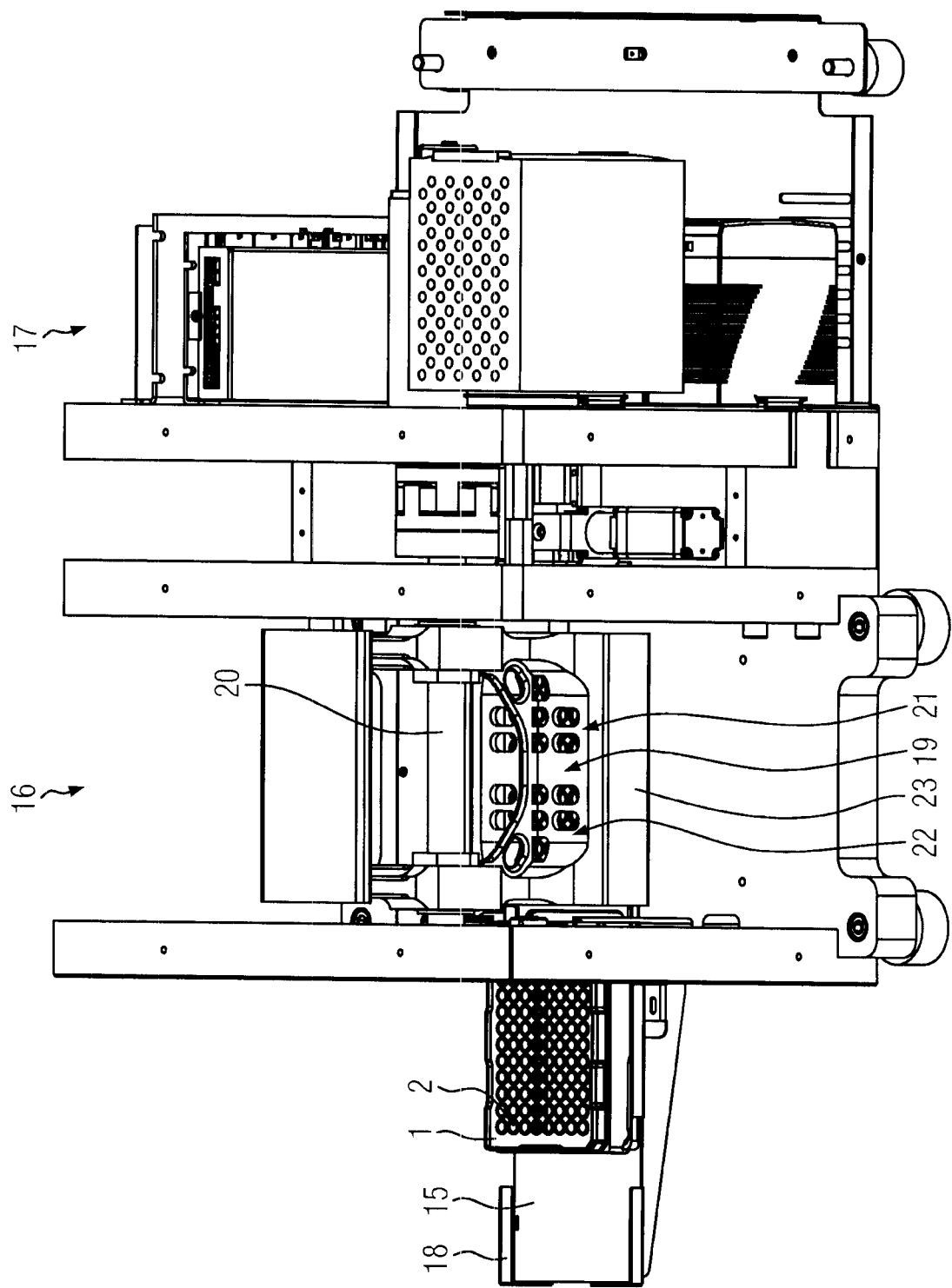

The centrifuge section 16 comprises a rotor 19. The rotor 19 is mounted on a horizontal shaft 20 (FIG. 7). The rotor 19 comprises a receptacle section for receiving one microplate 1. The receptacle section is embodied as plate tray 21. The plate tray 21 is defined by a rectangular base wall 22 and two U-rails 23. The U-rails 23 are arranged opposite with their open sides. In the lowest position of the plate tray, the U-rails 23 are below the base wall 22. In FIG. 6 the plate tray 21 is partly cut out, so that the microplate 2 and the microplate carrier 26 held in the plate tray 21 are visible.

The distance of the plate tray 21 to a rotation axis 24 is preferably larger than the lateral extension of the reaction well unit, particularly at least 1.5 times or 2 times larger than the lateral extension of the reaction well unit.

Diametrically opposite to the receptacle section or plate tray 21, a counterweight 40 is fixed to flanges 39 by means of legs 41. A further plate tray could be provided instead of a counterweight 40, which is embodied for receiving a microplate or a microplate carrier together with a microplate to form an adjustable counterweight to the kind of microplate used in the plate tray 21.

An opening 29 in a front side wall 28 is embodied at the level of the lowest position of the plate tray 21, which is the loading position of the rotor 19. The front platform 15 is provided on the same level as the base wall 22 of the plate tray 21 in the loading position, so that a microplate or a microplate on a microplate carrier can slide from the front platform 15 onto the base wall 22 and vice versa, wherein the openings of the reaction well 2 of the microplate 1 are directed to a shaft 20 which holds the rotor 19.

In the present embodiment, the base walls 22, the U-rails 23 and the sections in between the base walls 22 are made from one single piece of aluminum.

On the front side of the rotor 19, the plate trays 21 are open so that a microplate can slide into the plate tray 21. At the rear side of the rotor 19, a stopper 25 is provided. The stopper 25 comprises preferably a magnetic element.

The section in between the base walls 22 is cut out as far as possible and bores are provided in the base walls 22 to minimize the moment of inertia.

In the present embodiment, the plate tray 21 is designed for receiving a microplate 1 together with a microplate carrier 26. The microplate carrier 26 is a rectangular frame having rims 42 at the side edges, wherein the inner surfaces of the rims define the position of a microplate on the microplate carrier 26 with a small play. The upper surfaces of the rims 42 are tilted inwardly so that a microplate is sliding into the section which is defined by the rims.

The microplate carrier 26 comprises at one side edge a coupling element 43 made of magnetic material, particularly of a ferromagnetic material. This coupling element 27 can cooperate with the magnetic stopper 25 on the rotor 19.

The opening 29 in front side wall 28 has the form of a rectangular slid. An automatic door is provided for closing the opening 29. The opening 29 is arranged in the level of the front platform 15. In the loading position, the rotor 19 is arranged horizontally with its base walls 22, wherein the base wall of the plate tray 21 is arranged on the same level as the front platform 15, so that a microplate carrier 26 and a microplate 1 can slide horizontally from the front platform 15 into the lower plate tray 21 and vice versa.

On the upper edge of the opening, pipetting nozzles are provided for dispensing reagents into the reaction wells 2 of the microplate 1.

In the gap between the front platform 15 and the rotor 19, an upper line camera 44 is disposed above the transportation path of the microplate with its viewing direction downwards onto the top surface of the microplate 1. A lower line camera 45 is disposed below the transportation path of the microplate with its viewing direction up-wards onto the bottom surface of the microplate 1 (FIG. 5). When the microplate 1 is moved through the opening 29, images of the complete upper and lower sides of the microplate 1 can be detected by the line cameras 44, 45.

The driving section 17 comprises a motor (not shown) for rotating the shaft 20 and the rotor 19. The motor is connected to a control unit for controlling the rotation speed. This centrifuge is designed for centrifuging a microplate 1. As the distance between the microplate and the shaft 20 or rotation axis 24 is large, nearly the same centrifugal acceleration is exerted to the fluid in the different reaction wells 2. Therefore, the same centrifugation effect is achieved independently of whether the fluid is located in a center reaction wells or a lateral reaction well.

A control unit is provided to control the speed as well as the acceleration of the rotor. The speed of the rotor is in the range of 100 RPM to 3,000 RPM. The acceleration and deceleration of the rotor lies in the range of 100-1,200 RPM/s. When starting the rotor, it shall be accelerated, so that, after a turn of about 180°, at least a centrifugal acceleration of 1 g should be applied, so that no fluid drops out of the reaction wells with its openings directing downwardly. Microplates having deep well reaction wells can be accelerated as fast as possible. However, accelerating microplates with small wells as reaction wells could cause a contamination by sloshing of fluid from one reaction wells to a neighboring reaction well due to the acceleration. The danger of such a sloshing contamination depends on the filling amount of the reaction wells as well as on the form of the reaction wells. It has been shown that with an acceleration up to 500 RPM/s to 1,200 RPM/s, no contamination due to sloshing occurs.

The driving section 17 also comprises a loading mechanism 30 for loading and unloading the centrifuge 14 with a microplate 1.

A loading mechanism 30 comprises a flexible elongated beam 31 for extension and retraction of a microplate 1 or a microplate carrier 26 together with a microplate 1 (FIG. 5). The flexible elongated beam 31 is made of a stripe of metal sheet which is slightly bent transverse to its longitudinal extension. Thus, the metal sheet provides certain stiffness if it is extended linearly and on the other hand it can be bent around an axis transverse to the longitudinal extension. Such bent metal sheet stripes are well known from metal measuring tapes.

In the present embodiment, one end of the beam 31 is fixed vertically at an inner wall 32 of the driving section 17, wherein the beam is extending from the inner wall 32 rearwards. The beam 31 is bent by a U-turn, so that a free end 33 of the beam is directed forwardly and the beam is extending through a slid in the inner wall 32. Thus, the beam comprises an upper strand 34 fixed to the inner wall 32 and a lower strand 35 extending through the slid of the inner wall 32. The strand 35, which is extending through the inner wall 32 and which comprises the free end 33, is clamped between two wheels (not shown), wherein one of the two wheels is driven by a stepper motor 37. Only one of the two wheels is shown in the drawings. The free end 33 of the beam 31 is provided with a magnetic element 38. The beam 31 can be actuated by means of the stepper motor 37 so that the free end 33 with its magnetic element 38 is extended or driven through the centrifuge section 16 and through the opening 29 in the front side wall 28. Thus, the free end 33 of the beam 31 reaches the area of the front platform 15 in the maximum extended position. In the maximum retracted position, the free end 33 of the beam 31 is arranged behind the rotor 19 and particularly out of the centrifuge section 16, so that the rotor 19 can be freely rotated.

The loading mechanism 30 can be coupled to a microplate carrier 26, which is placed on the front platform 15, just by extending the beam 31 until the magnetic element 38 of the beam couples through the coupling element 27 of the microplate carrier 26. By retracting the beam 31, the microplate carrier 26 is drawn into one of the plate trays 21 of the rotor 19. When the microplate carrier 26 abuts to the stopper 25, the coupling between the magnetic element 38 of the beam 31 and the coupling element 27 of the microplate carrier 26 is released by further retracting the beam and simultaneously the coupling element 27 of the microplate carrier 26 is coupled to the magnetic element of the stopper 25 and thus fixed in position in the rotor 19.

This loading mechanism 30 allows coupling the centrifuge 14 to any transport system for transporting microplates in an automatic labor robot. The labor robot just has to put a microplate 1 onto a microplate carrier 26 located at the front platform 15. Then the loading mechanism 30 can load and unload the rotor 19. It is also possible to place the centrifuge 14 without a front plate directly adjacent to a transport belt for transporting microplates, wherein microplates 1 can be withdrawn from the transport belt with the loading mechanism 30 and can be put onto the transport belt again. In the present embodiment, a microplate carrier 26 having a coupling element 27 is used. It is also possible to provide the microplates 1 with such coupling elements 27, so that there is no need for a microplate carrier.

A further advantage is that the loading mechanism 30 is placed on the rear side of the centrifuge section 16, so that the centrifuge 14 can be coupled to an existing laboratory robot without any intermediate devices. This facilitates the integration of the centrifuge into existing laboratory robots.

In the following, the use of the above-described microplate 1 in the testing apparatus 13 is described for determining the result of one or more agglutination reactions.

The method starts preferably with an empty microplate 1. The reaction wells 2 are filled by means of a pipetting device with a gel material. For each agglutination reaction which is to be carried out, an individual reaction well 2 is filled with gel material. If the number of agglutination reactions is smaller than the number of reaction wells 2 provided in one microplate, then the reaction wells which are not needed are not filled with gel material.

After filling the respective reaction wells with each a specific amount of gel material, the microplate is centrifuged to force the gel material to the lower portion of the reaction wells, so that the gel material fills the collection section and a major part of the separation section 7 without containing any air bubble.

Due to the centrifugation step, it is possible to fill the reaction wells on site with gel material, even if reaction wells with small diameter are used. There is no need for reaction wells which are preloaded with separation material. Of course, it is also possible to use preloaded reaction wells.

The reaction wells containing separation material are loaded with a suspension containing a specific reagent. Different reaction wells can be loaded with different reagents. The reagents typically comprise an antigen or antibody or blood cells of a known blood type.

A certain amount of a sample under test is dispensed in the reaction wells containing the separation material and the reagent. Preferably, the sample material of the same sample is distributed to reaction wells containing different reagents and material of different samples can be distributed to different groups of reaction wells. Thus, it is possible to simultaneously test a plurality of different samples, wherein each sample is tested with respect of a plurality of different reagents.

The microplate containing reaction wells loaded with samples, reagents and separation material is incubated, wherein a certain temperature is applied for a predetermined duration. This incubation step can be carried out in a separate incubator. Optionally, the centrifuge comprises a heating means, so that the microplate can be incubated in the centrifuge. Thereafter, the microplate is centrifuged, wherein the non-agglutinated sample parts penetrate the gel material in the direction to the bottom wall 4 of the reaction wells 2. The non-agglutinated parts of the sample are collected in the collection section 10 of the reaction wells 2. If the result of the agglutination reaction is that an agglutination took part, then the agglutinated sample material maintains on the top side of the separation material (FIG. 4a). If there is only a weak agglutination reaction or a retarded agglutination reaction, then agglutinated clumps are small and are stopped inside the gel-material and do not reach the bottom wall 4 or the collection section 10 of the reaction wells 2. The agglutinated gel material is retained in the gel material and distributed therein, as it can be seen in FIGS. 4b and 4c. The weaker the agglutination reaction is, the larger is the number of non-agglutinated sample parts and the more sample parts reach the collection section 10, as it can been in FIG. 4d-4f.

After the centrifugation step, the microplate is discharged from the centrifuge, wherein images are taken from the top side and the bottom side of the reaction wells with the line camera.

The FIGS. 4a-4f each show a picture of the top side above the respective reaction well 2 and a picture of the bottom side below the respective reaction well. The gray levels of these two pictures are automatically compared, wherein the difference of the gray levels is calculated. There are five classes of results, namely 0, 1+, 2+, 3+, and 4+. Each level of difference is assigned to a certain class, wherein if there is only agglutinated sample material, then the top side of the reaction well is dark and the bottom side of the reaction well is light and the corresponding class is 4+ and if the agglutination reaction is very weak, then all or nearly all sample parts reach the collection section 10 and the bottom side of the reaction well is dark and the top side is light (FIG. 4, 40, wherein the class is 0 (=no agglutination reaction).

If the sample material comprises red blood cells, then preferably color images are taken and the color intensity of the color red of the image of the top side and the bottom side are compared.

In the present embodiment, the cross sectional area of the opening 3 of the reaction well 2 has the form of a square and the collection section 10 has the cross sectional form of a circle. Thus, the pictures taken from the top side show a square and the pictures taken from the bottom side show a circle. By the form of the detected pattern (circle or square), it can be judged whether the picture is from the top side or the bottom side of the reaction well. This ensures that, if the pictures are manually controlled, the pictures of the bottom side and the top side are not mixed with each other. Therefore, it is preferable that the forms of the opening 3 and the collection section 10 of the reaction wells 2 differ.

The absolute color intensities or gray levels depend on a plurality of circumstances, such as background light, type of separation material, amount of sample material dispensed into each reaction well, etc. By comparing the images of the top side and the bottom side of the reaction wells, these influences are eliminated, because the decision whether there is an agglutination reaction or whether there is no agglutination reaction is only based on the difference of the color intensity and/or gray level of the two images. This makes the test very reliable and stable. Furthermore, it is easy to calibrate the tests on different separation materials and different reagents, so that the overall process is very flexible. This system is particularly suitable for testing huge amounts of samples with a high throughput and at low costs.

In the above described embodiment, the color intensities and/or gray levels of the two images of the top side and the bottom side of the reaction well are compared. Additionally, the images can be compared with predetermined sample images.

LIST OF REFERENCES 1 microplate
25 stopper
2 reaction well
26 microplate carrier
3 opening
30 27 coupling element
4 bottom wall
28 front side wall
5 filing section
29 opening
6 transfer section
30 loading mechanism
7 separation section
31 flexible elongated beam
8 upper part
35 32 inner wall
9 lower part (conical portion)
33 free end
0 collection section
34 upper strand
1 frame
35 lower strand
2 side wall
36 3 testing apparatus
40 37 stepper motor
4 centrifuge
38 magnetic element
5 front platform
39 flange
6 centrifuge section
40 counterweight
7 driving section
41 leg
8 rim
45 42 rim
9 rotor
43 pipetting nozzle
0 shaft
44 upper line camera
1 plate tray
45 lower line camera
2 base wall
3 U-rail
50 4 rotation axis

The invention claimed is:

1. Microplate for determining products of agglutination reactions having a plurality of wells arranged in a two-dimensional array, wherein
at least one of said wells comprises a separation section which operatively contains a separation material comprising a gel or a bead matrix, wherein
the separation section comprises at least one conical portion which is tapered downwards, so that sample material penetrating the separation material will be concentrated to the center of the respective well; and
wherein the separation section comprises a reaction part that has a cross sectional area in the form of a square; and
wherein the wells comprise a collection section that has a cross sectional area in the form of a circle.

2. Microplate according to claim 1, wherein the collection section is for collecting the sample material penetrating the separation material at a bottom end of the well.

3. Microplate according to claim 2, wherein the separation section comprises a hollow cylinder.

4. Microplate according to claim 3, wherein the wells comprise a filling section at the top end of the wells, wherein the cross sectional area of the filling section is larger than the cross sectional area of the separation section.

5. Microplate according to claim 4, wherein the microplate comprises at least 96 wells, and/or, wherein the inner height of the reaction wells is between 5 mm and 20 mm.

6. Microplate according to claim 1, wherein the separation section comprises a hollow cylinder.

7. Microplate according to claim 2, wherein the wells comprise a filling section at the top end of the wells, wherein the cross sectional area of the filling section is larger than the cross sectional area of the separation section.

8. Microplate according to claim 1, wherein the microplate comprises at least 96 wells, and/or, wherein the inner height of the reaction wells is between 5 mm and 20 mm.

9. Microplate for determining products of agglutination reactions having a plurality of wells arranged in a two-dimensional array, wherein at least one of said wells comprises
a filling section;
a transfer section below the filling section, that tapers inwardly downward to;
a separation section which operatively contains a separation material comprising a gel or a bead matrix, wherein the separation section comprises at least one square-shaped upper part followed by conical portion that tapers inwardly to a downwards lower portion; and
a circle-shaped collection section, wherein sample material that operatively penetrates the separation material will be concentrated to the center of the respective well;
wherein the collection section has a cross sectional area shape that is distinct from a cross sectional area shape of the separation section when viewed along a longitudinal axis of the at a least one well.

10. Microplate according to claim 9, wherein the collection section is for collecting the sample material penetrating the separation material at a bottom end of the well.

11. Microplate according to claim 9, wherein the separation section comprises a hollow cylinder.

12. Microplate according to claim 9, wherein the microplate comprises at least 96 wells, and/or, wherein the inner height of the reaction wells is between 5 mm and 20 mm.

* * * * *